United States Patent [19]

Biedermann et al.

[11] Patent Number: 4,746,660

[45] Date of Patent: May 24, 1988

[54] PROCESS FOR REDUCING REFLEX TACHYCARDIA IN THE TREATMENT OF HYPERTENSION EMPLOYING A COMBINATION OF A DIAZACYCLOPENTENE DERIVATIVE AND A PYRIDAZINONE DERIVATIVE

[75] Inventors: Jürgen Biedermann, Pulheim-Stommeln; Harald Borbe, Cologne; Erich Graf, Kerpen; Gerd Hilboll; Gerrit Prop, both of Pulheim, all of Fed. Rep. of Germany

[73] Assignee: A. Natternabb & CIE GmbH, Cologne, Fed. Rep. of Germany

[21] Appl. No.: 5,622

[22] Filed: Jan. 21, 1987

Related U.S. Application Data

[62] Division of Ser. No. 705,668, Feb. 26, 1985, Pat. No. 4,661,487.

[30] Foreign Application Priority Data

Mar. 1, 1984 [DE] Fed. Rep. of Germany ....... 3407509

[51] Int. Cl.$^4$ ................. A61K 31/415; A61K 31/495
[52] U.S. Cl. ..................................... 514/252; 514/401
[58] Field of Search ................. 514/252, 401

[56] References Cited

U.S. PATENT DOCUMENTS 4,518,783 5/1985 Biedermann et al. ............... 548/353
4,643,998 2/1987 Hilboll et al. ...................... 514/252

OTHER PUBLICATIONS

Derwent Publication 67658x/36 of German Patent 1,795,843, 1 page (1968).

Primary Examiner—Allen J. Robinson
Attorney, Agent, or Firm—Pearne, Gordon, McCoy & Granger

[57] ABSTRACT

The invention relates to a new process for the treatment of hypertension and thromboembolic diseases in humans by simultaneous administration of (±)- or (−)-2-[1-(2,6-dichlorophenoxy)-ethyl]-1,3-diazacyclopent-2-ene hydrochloride on the one side, and 4,5-dihydro-6-[4-(1-imidazolyl)-phenyl]-5-methyl-3(2H)-pyridazinone or 4,5-dihydro-6-[4-(1-imidazolyl)-thien-2-yl]-5-methyl-3(2H)-pyridazinone, on the other side, as the active substances.

2 Claims, No Drawings

PROCESS FOR REDUCING REFLEX TACHYCARDIA IN THE TREATMENT OF HYPERTENSION EMPLOYING A COMBINATION OF A DIAZACYCLOPENTENE DERIVATIVE AND A PYRIDAZINONE DERIVATIVE

This is a division of application Ser. No. 705,668, filed Feb. 26, 1985, now U.S. Pat. No. 4,661,487, dated Apr. 28, 1987.

The invention relates to a new process for the treatment of hypertension and thromboembolic diseases in humans comprising administering to the human suffering from such state or disease a medicament containing (±)- or (−)-2-[1-(2,6-dichlorophenoxy)-ethyl]-1,3-diazacyclopent-2-ene hydrochloride, on the one side, and in combination therewith, a compound of the formula I

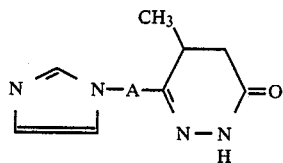

wherein A denotes 1,4-phenylene or 2,4- or 2,5-thienylene, on the other side, as the active constituents.

The therapy of hypertension with substances which exert their action, above all, via peripheral vasodilation, which is associated with reflex tachycardia, is known. Besides the known products employed in hypertension therapy, that is to say hydralazine, dihydralazine and minoxidil, the hypotensive, platelet aggregation-inhibiting and antithrombotic 4,5-dihydro-3(2H)-pyridazinones of the formula I also show this side effect.

It has now been found that the undesired reflex increase is heart rate can be reduced, avoided entirely or even partly reversed into bradycardia when one of the compounds of the formula I is combined with (±)-2-[1-(2,6-dichlorophenoxy)-ethyl]-1,3-diazacyclopent-2-ene hydrochloride (German Patent Specification No. 1,795,843, generic name: lofexidine) or (−)-2-[1-(2,6-dichlorophenoxy)-ethyl]-1,3-diazacyclopent-2-ene hydrochloride (German Offenlegungsschrift No. 3,149,009, generic name: laevlofexidine), which are known as antihypertensives, the antihypertensive effect in some cases being increased further and lasting longer. The platelet aggregation-inhibiting and antithrombotic action of the compounds of the formula I is not reduced by this combination.

Thus, the present invention is directed to a process for the treatment of hypertension and thromboembolic diseases in humans comprising administering to the human suffering from such state or disease a medicament containing as active principle a combination of a member selected from the group consisting of (±)- and (−)-2-[1-(2,6-dichlorophenoxy)-ethyl]-1,3-diazacyclopent-2-ene hydrochloride, on the one side, and a compound of the formula I, wherein A is a member selected from the group consisting of the 1,4-phenylene, 2,5-thienylene and 2,4-thienylene groups, on the other side.

Particularly suitable 4,5-dihydro-3(2H)-pyridazinones of the formula I in the combinations according to the invention are: 4,5-dihydro-6-[4-(1-imidazolyl)-phenyl]-5-methyl-3(2H)-pyridazinone, 4,5-dihydro-6-[4-(1-imidazolyl)-thien-2-yl]-5-methyl-3(2H)-pyridazinone and 4,5-dihydro-6-[5-(1-imidazolyl)-thien-2-yl]-5-methyl-3(2H)-pyridazinone, in particular 4,5-dihydro-6-[4-(1-imidazolyl)-phenyl]-5-methyl-3(2H)-pyridazinone and 4,5-dihydro-6-[4-(1-imidazolyl)thien-2-yl]-5-methyl-3(2H)-pyridazinone.

Pharmaceutically acceptable salts of the compounds of the formula I with inorganic or organic acids are also included, for example and in particular the hydrochlorides, methanesulphonates, sulphates, acetates, fumarates, benzoates and citrates.

The compounds of the formula I are mentioned in German Offenlegungsschrift DE-OS No. 3,212,304, and in published European patent application EP No. 75,436, and they can be prepared by processes described therein or analogous thereto.

The medicament combinations according to the invention contain the particular compound of the formula I and (±)-lofexidine or (−)-lofexidine in a weight ratio of 500:1 to 10:1, preferably in a ratio of 150:1 to 30:1.

The present invention also relates to pharmaceutical products which contain the active compound combinations according to the invention or pharmaceutically useful acid addition salts thereof. The pharmaceutical products according to the invention are those for enteral, such as oral or rectal, and parenteral administration, which contain the pharmaceutical active compound combination by itself or together with a customary pharmaceutically usable excipient. The pharmaceutical formulation of the active compound combination is advantageously in the form of individual doses which are matched to the desired administration, such as, for example, tablets, coated tablets, capsules, suppositories, granules, solutions, emulsions or suspensions.)

The pharmaceutical products according to the present invention are produced in usual manners by mixing the active substances in the above weight ratio with the pharmaceutically usable excipients for the desired form of administration and converting this mixture into the desired form of administration.

The dosage of the active compound combination is usually between 1 to 500 mg per dose, preferably between 3 to 150 mg per dose in the case of oral administration, and can be administered once or several times, preferably two or three times, daily.

The pharmacological advantages of the active compound combinations according to the invention are illustrated in more detail by the following examples.

EXAMPLE 1

Hypotensive and heart rate-modifying action of the combination of 4,5-dihydro-6-[4-(1-imidazolyl)-phenyl]-5-methyl-3(2H)-pyridazinone (B) and lofexidine (A) on SHR rats.

Method

The substances were administered orally with a probang to fasting spontaneously hypertensive rats. The animals were fasted 17 hours before the start of the experiment.

All the substances were dissolved in 1% strength carboxymethylcellulose (MH 300), and the administration volume was 10 ml/kg.

The starting values of the blood pressure and heart rate were recorded directly before the administration. The action of the substance was measured 1, 2, 4, 7 and 24 hours after the administration.

The measurement was performed non-invasively with a W+W Recorder 8002, it being possible to measure the systolic blood pressure and the heart rate. The animals were offered food again 4 hours after administration of the substance. The values can be seen from Table 1, page 5.

TABLE 1

| Dosage (mg/kg) p.o. of substance | | Starting value | Δ after administration of the substance | | | | |
|---|---|---|---|---|---|---|---|
| A | B | | 1 | 2 | 4 | 7 | 24 hours |
| | | | Systolic blood pressure (mmHg) | | | | |
| 0.1 | — | 221.0 ± 12.5 | −18.8 ± 16.6 | −4.0 ± 18.6 | −11.8 ± 23.2 | −10.8 ± 26.9 | — |
| 1.0 | — | 231.0 ± 16.9 | −28.4 ± 13.1 | −22.8 ± 11.8 | −23.6 ± 15.5 | −22.2 ± 17.4 | — |
| — | 10.0 | 210.0 ± 4.6 | −95.4 ± 3.4 | −97.2 ± 4.6 | −98.4 ± 5.6 | −93.0 ± 5.6 | −35.8 ± 6.6 |
| 0.1 | 10.0 | 213.0 ± 15.5 | −99.4 ± 11.4 | −102.8 ± 11.9 | −105.6 ± 10.9 | −105.0 ± 15.4 | −59.8 ± 7.6 |
| 1.0 | 10.0 | 246.0 ± 18.4 | −87.2 ± 6.6 | −83.8 ± 13.9 | −109.2 ± 14.7 | −126.6 ± 13.4 | −120.8 ± 26.4 |
| | | | Heart rate (beats/minute) | | | | |
| 0.1 | — | 357 ± 10 | +10 ± 13 | +37 ± 27 | +12 ± 12 | −14 ± 12 | — |
| 1.0 | — | 353 ± 11 | −22 ± 8 | −6 ± 13 | −2 ± 15 | −10 ± 16 | — |
| — | 10.0 | 354 ± 13 | +113 ± 14 | +108 ± 10 | +85 ± 21 | +129 ± 24 | +16 ± 16 |
| 0.1 | 10.0 | 422 ± 17 | −19 ± 22 | −42 ± 23 | −56 ± 18 | −44 ± 22 | −10 ± 16 |
| 1.0 | 10.0 | 410 ± 17 | −133 ± 9 | −144 ± 16 | −148 ± 21 | −134 ± 25 | +2 ± 32 |

EXAMPLE 2

Hypotensive and heart rate-modifying action of the combination of 4,5-dihydro-6-[4-(1-imidazolyl)thien-2-yl]-5-methyl-3(2H)-pyridazinone (C) and lofexidine (A) on SHR rats. The experiment was carried out by the same method as in Example 1, and the values can be seen in Table 2.

TABLE 2

| Dosage (mg/kg) p.o. of substance | | Starting value | Δ after administration of the substance | | | |
|---|---|---|---|---|---|---|
| A | C | | 1 | 2 | 4 | 7 |
| | | | Systolic blood pressure (mmHg) | | | |
| 0.1 | — | 211.0 ± 12.5 | −18.8 ± 16.6 | −4.0 ± 18.6 | −11.8 ± 23.2 | −10.8 ± 26.9 |
| 1.0 | — | 231.0 ± 16.9 | −28.4 ± 13.1 | −22.8 ± 11.8 | −23.6 ± 15.5 | −22.2 ± 17.4 |
| — | 10.0 | 185.0 ± 3.5 | −48.1 ± 16.2 | −66.2 ± 9.9 | −93.9 ± 6.8 | −98.9 ± 9.1 |
| 0.1 | 10.0 | 182.6 ± 10.1 | −58.8 ± 9.4 | −55.0 ± 9.4 | −71.0 ± 12.3 | −11.6 ± 13.9 |
| 1.0 | 10.0 | 221.2 ± 10.1 | −91.0 ± 12.4 | −103.0 ± 11.9 | −111.6 ± 10.9 | −73.0 ± 12.2 |
| | | | Heart rate (beats/minute) | | | |
| 0.1 | — | 357 ± 10 | +10 ± 13 | +37 ± 27 | +12 ± 12 | −14 ± 12 |
| 1.0 | — | 353 ± 11 | −22 ± 18 | −6 ± 13 | −2 ± 15 | −10 ± 16 |
| — | 10.0 | 389 ± 13 | +104 ± 21 | +91 ± 10 | +70 ± 12 | +36 ± 13 |
| 0.1 | 10.0 | 396 ± 15 | +71 ± 8 | +41 ± 13 | +61 ± 13 | +17 ± 22 |
| 1.0 | 10.0 | 367 ± 9 | +24 ± 29 | +17 ± 16 | +10 ± 24 | +60 ± 35 |

EXAMPLE 3

Inhibition of the collagen-induced aggregation of human platelets by the combination of 4,5-dihydro-6-[4-(1-imidazolyl)-thien-2-yl]-5-methyl-3(2H)-pyridazinone hydrochloride (D) with lofexidine (A).

The inhibition of collagen-induced platelet aggregation in vitro was carried out by the method of Born (Nature, 194, 927–929 (1962)) on platelet-rich human plasma with 4,5-dihydro-6-[4-(1-imidazolyl)-thien-2-yl]-5-methyl-3(2H)-pyridazinone hydrochloride (D), lofexidine (A) and with mixtures of A and D.

The concentration for a half-maximum inhibition (IC$_{50}$) of the collagen-induced platelet aggregation was determined as a comparable measurement parameter. In each case the mean value of 4 independent determinations has been given. In the investigations of the mixtures, the concentration of A was constant at $1 \times 10^{-5}$ mole/l. The results are summarised in Table 3.

TABLE 3

| Substance [mole/l] | | % inhibition |
|---|---|---|
| A | D | |
| $1 \times 10^{-5}$ | 0 | 3 |
| 0 | $4.6 \times 10^{-8}$ | 50 |
| $1 \times 10^{-5}$ | $5.2 \times 10^{-8}$ | 50 |

EXAMPLE 4

Pharmaceutical form of the combination according to the invention:

Tablets weighing 150 mg with an active compound content of 0.05 mg of the imidazoline compound and 5 mg of the pyridazine compound.

(±)-2-[1-(2,6-dichlorophenoxy)-ethyl]-1,3-diazacyclopent-2-ene hydrochloride: 0.003 kg
4,5-dihydro-6-[4-(1-imidazolyl)-thien-2-yl]-5-methyl-3(2H)-pyridazinone: 0.300 kg
Avicel: 7.287 kg
citric acid: 1.200 kg
Aerosil: 0.120 kg
magnesium stearate: 0.090 kg

What we claim is:
1. Process for reducing reflex tachycardia occurring in the treatment of hypertension and thromboembolic diseases in humans with compounds of formula I

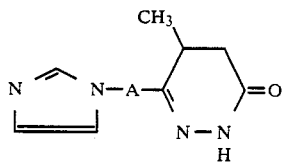

wherein A is a member selected from the group consisting of the 2,5-thienylene and 2,4-thienylene groups, comprising administering to the humans an effective amount of a combination of the compound of formula I and a compound selected from the group consisting of (±)- and (−)-2-[1-(2,6-dichlorophenoxy)-ethyl]-1,3-diazacyclopent-2-ene hydrochloride in a weight ratio of from 150:1 to 10:1.

2. The process as claimed in claim 1, wherein the weight ratio is 100:1 to 30:1.

* * * * *

UNITED STATES PATENT AND TRADEMARK OFFICE
CERTIFICATE OF CORRECTION

PATENT NO. : 4,746,660

DATED : May 24, 1988

INVENTOR(S) : Jurgen Biedermann et al.

It is certified that error appears in the above-identified patent and that said Letters Patent is hereby corrected as shown below:

On the cover page of the patent, Section [73] Assignee should read as follows:

--[73] Assignee: A. Nattermann & Cie GmbH, Fed. Rep. of Germany--

Signed and Sealed this

First Day of August, 1989

Attest:

DONALD J. QUIGG

Attesting Officer

Commissioner of Patents and Trademarks